United States Patent
Bluman

(10) Patent No.: US 8,485,996 B2
(45) Date of Patent: Jul. 16, 2013

(54) METHOD AND SYSTEM FOR MOTION IMPROVEMENT

(75) Inventor: Nini Bluman, Rehovot (IL)

(73) Assignee: Bioxtreme Ltd., Ashkelon (IL)

( * ) Notice: Subject to any disclaimer, the term of this patent is extended or adjusted under 35 U.S.C. 154(b) by 1052 days.

(21) Appl. No.: 10/554,501

(22) PCT Filed: May 2, 2004

(86) PCT No.: PCT/IL2004/000365
§ 371 (c)(1),
(2), (4) Date: Sep. 28, 2006

(87) PCT Pub. No.: WO2004/096501
PCT Pub. Date: Nov. 11, 2004

(65) Prior Publication Data
US 2007/0060849 A1    Mar. 15, 2007

Related U.S. Application Data

(60) Provisional application No. 60/466,464, filed on Apr. 30, 2003.

(51) Int. Cl.
*A61H 1/00*    (2006.01)

(52) U.S. Cl.
USPC .............................................. 601/33; 601/23

(58) Field of Classification Search
USPC ............... 601/5, 23, 33; 482/9, 901; 600/587, 600/595
See application file for complete search history.

(56) References Cited

U.S. PATENT DOCUMENTS

| | | | |
|---|---|---|---|
| 4,354,676 A | | 10/1982 | Ariel |
| 4,544,154 A | | 10/1985 | Ariel |
| 5,078,152 A | * | 1/1992 | Bond et al. ..................... 601/33 |
| 5,387,170 A | | 2/1995 | Rawls et al. |
| 5,409,435 A | | 4/1995 | Daniels |
| 5,466,213 A | | 11/1995 | Hogan et al. |
| 5,830,160 A | * | 11/1998 | Reinkensmeyer ............ 600/595 |
| 6,155,993 A | | 12/2000 | Scott |
| 6,413,195 B1 | | 7/2002 | Barzelay |
| 2008/0077057 A1 | * | 3/2008 | Peles ................................ 601/5 |

OTHER PUBLICATIONS

H.I. Krebs, et al., "Robot-Aided Neurorehabilitation"; IEEE Transactions on Rehabilitation Engineering, vol. 6, No. 1, Mar. 1998.
Supplementary Partial European Search Report mailed Aug. 6, 2008.

* cited by examiner

*Primary Examiner* — Quang D Thanh
(74) *Attorney, Agent, or Firm* — Browdy and Neimark, PLLC

(57) ABSTRACT

A method and system are presented for improving the object's motion. Data indicative of a measured motion of the object is processed, and a relation between the measured motion and a predetermined correct motion is determined. This relation is indicative of an error in the measured motion. Based on the determined error, an operating signal may be generated to be used to apply an effecting force to the object. The operating signal is such that the effecting force, when applied to the object, will increase a value of the error in the object's motion.

46 Claims, 9 Drawing Sheets

METHOD AND SYSTEM FOR MOTION IMPROVEMENT

FIELD OF THE INVENTION

This invention relates to an automatic system and method for control and improvement of motion, and is particularly useful for improving motion capabilities of human beings and animals.

BACKGROUND OF THE INVENTION

In order to rehabilitate people who suffer from movement disorders, various kinds of therapies are employed such as neurotherapy, physical therapy, etc. Changes in motion capabilities, in general, can be obtained either by biomechanical changes (e.g., using drugs to build muscles, anaerobic, aerobic, performing work against force), or by repeated practice against a predetermined target, teaching and guiding, before, during or after the practice. Both theses techniques might be based on practicing the movement as it is, without any external facilities, or with facilities such as physicians, computer games, virtual reality, etc. Usually, these techniques are time consuming. Consequently, the capacity to handle therapy for example by physicians, who perform such therapies, is significantly limited.

It is noted that most of the existing devices of the kind specified are capable of mainly changing and possibly improving motion capabilities by biomechanical changes.

An example of the existing devices is disclosed for example in U.S. Pat. No. 4,354,676. According to this technique, an exerciser bar is supported for rotation and acts against an hydraulic cylinder with the angle of the bar and the pressure in the cylinder measured and fed to a micro computer which, using this input data, controls the cylinder pressure in accordance with a selected exercise program, the micro computer also providing outputs to displays so that the person exercising can monitor his progress.

U.S. Pat. No. 4,544,154 discloses a passive programmable resistance device that uses a closed loop feedback for controlling resistance to rotational or translational motion of an object. One or more actual parameters, such as force or position, are measured and compared with desired parameters. The differences are used to provide a control signal which controls the resistance to the movement of the object.

U.S. Pat. No. 5,466,213 discloses an interactive robotic therapist that interacts with a patient to shape the motor skills of the patient by guiding the patient's limb through a series of desired exercises with a robotic arm. The patient's limb is brought through a full range of motion to rehabilitate multiple muscle groups. A drive system coupled to the robotic arm is controlled by a controller which provides the commands to direct the robotic arm through the series of desired exercises. This robot is further described in a website http://www.interactive-motion.com/ and in a paper "Robot-Aided Neurorehabilitation", Hermano Igo Krebs, Neville Hogan, Mindy L. Aisen, and Bruce T. Volpe, IEEE Transactions on Rehabilitation Engineering, Vol. 6, No. 1, March 1998.

U.S. Pat. No. 6,413,195 discloses a passive/active hydraulic exercise device having a base portion, an upright support and a pivot bard that is selectively placed in either a passive push and pull type resistance mode or an active velocity type mode. In the passive mode, a pump can be off or on during "idling". A solenoid valve is energized to an open position, and a servo valve sets a resistance for the fluid flow in the system. A check valve compensates for the differential areas of the cylinder. The active mode is useful for physical therapy applications. In this mode, a constant cycling operation is provided at absolute minimum force levels. The load cell senses the actual force generated, and the position feedback senses actual movement of the exercise bar. As long as the subject is providing enough force to move the bar, the feedback device confirms movement to the computer which adjusts the resistance of the electronic pressure control valve to a value which will allow the subject to continue moving the bar. This force is measured by the load cell and controlled by the servo-valve.

SUMMARY OF THE INVENTION

There is a need in the art to facilitate controlling a motion carried out by an object to improve this motion.

Here the term "object" signifies a human or animal body (e.g., pets, husbandry animals), as well as a machine (e.g., robot).

The main idea of the present invention consists of controlling the object's motion so as to allow affecting this motion in a manner to cause the object (e.g., patient) to improve the motion. The motion improvement of the present invention is based on assessment of a relevant motion parameter and predetermined data. The present invention provides for the motion control analysis and especially for the functional movement disorders detection.

For the purpose of this invention, the term "motion" signifies any displacement of an object or a part thereof. As indicated above, an object can be human being, an animal or a machine. These may be people who were born with movement disorders, or being physically rehabilitated. These can also be sportsmen, people who will to improve their movement skill. The motion performance is usually characterized by the following parameters: force, acceleration, speed, accuracy, stability, repeatability, range of movement, and fatigue-less work. Improving the (measured) value of any of these parameters will be referred herein as "motion improvement". Also of use here is the term "motion control" that signifies the ability to regulate or direct the mechanisms essential to movement. The term "force" used herein signifies any effect that drives, moves, changes the object position, etc. These include a direct force, torque, moment, etc.

According to one aspect of the present invention, there is provided a method for use in improving the object's motion, the method comprising: processing data indicative of a measured motion of the object and determining a relation between the measured motion and a predetermined correct motion, said relation being indicative of an error in said measured motion; thereby enabling generation of an operating signal to be used to apply an effecting force to said object, said operating signal being such that said effecting force, when applied to the object, will increase a value of said error.

The operating signal is such that the application of the effecting force will cause the object to initiate a negative motion relative to this force, and the resulting the object's motion will thus approach the correct motion. Preferably, the operating signal is such as to define at least one of one-dimensional, two-dimensional, and three-dimensional vectors of the effecting force.

The error may be indicative of a difference between the correct and the measured motions; or may be indicative of a ratio between the correct and the measured motions. Preferably, the effecting force is determined as a minimum between certain first and second force values, wherein the first force value is determined as a safety upper-limit force applicable to the object while preventing damage to the object during the monitoring, and the second force value is defined by the measured error so as to cause the increase of the error. The effecting force may be a resistive force only.

Preferably, upon determining the error, it is analyzed to determine whether a certain predefined motion condition is satisfied with respect to this error, to thereby generate the operating signal, if this condition is satisfied.

Preferably, the data indicative of the correct motion of the object is provided prior to monitoring. This may include providing a database including the correct motion data for various types of motions.

The data indicative of the measured motion of the object may comprise at least one physical parameter of the object, whose motion is to be improved, e.g., the object's weight and/or dimension. Similarly, the data indicative of the correct object's motion may comprise at least one physical parameter of the object, such as the object's weight and/or dimension. The method may utilize analyzing the generated data indicative of the measured motion to update the data indicative of the correct object's motion.

The monitoring may be carried out while substantially unaffecting the data indicative of the measured motion, or while providing a known effect on the data indicative of the measured motion, in which case the processing takes into account this known effect while determining the relation between the measured motion and the correct motion.

The method may utilize providing motion directions to the object, whose motion is to be improved.

According to another aspect of the invention, there is provided, a method for use in improving the object's motion, the method comprising:

(a) providing data indicative of a correct motion of the object;

(b) monitoring the motion of the object and generating data indicative of a measured motion;

(c) processing the generated data and determining a relation between said measured motion and said correct motion, said relation being indicative of an error in said measured motion;

(d) analyzing the determined error to enable generation of an operating signal defining an effecting force to be applied to the object, said operating signal being such that the effecting force when applied to the object increases a value of said error.

According to yet another aspect of the invention, there is provided a system for use in improvement of the object's motion, the system comprising:

a monitoring assembly configured and operable for monitoring;

motion of the object and generating data indicative of the measured motion;

a force applying assembly configured and operable to apply a force to the object;

a control unit having a memory utility for storing data indicative of a correct motion of the object; and a data processing and analyzing utility preprogrammed to analyze the data generated by the monitoring assembly, determining an error in the measured motion as a relation between the measured motion and the correct motion, to thereby enable generation of an operating signal to be used for operating the force applying assembly to apply to the object an effecting force, said operating signal being such that the effecting force, when applied to the object, will increase a value of said error.

The system may comprise a motion directing arrangement presenting motion instructions to a user, whose motion is to be improved.

The relation between the measured and correct motions may be determined as a difference between these motions; or as a ratio between them.

The system preferably comprises an interface assembly interconnected between the force applying assembly and the object. The interface assembly may be configured for holding the object whose motion is to be improved.

The interface assembly may be configured for substantially unaffecting the data indicative of the measured motion; or for applying a known effect on the data indicative of the measured motion, in which case the data processing and analyzing utility is preprogrammed to take into account this known effect while determining the relation between the measured motion and the correct motion.

The interface assembly may be configured to be operable in first and second modes: when operating with the first mode the interface assembly affects the motion of the object, and when operating with the second mode the interface assembly follows the object's motion. The interface assembly may be configured and operable to enable the object to conduct the motion; or configured and operable to transfer forces between the object, whose motion is to be improved, and a second object.

The monitoring assembly may be configured for measuring a time variations of a position of the object. The monitoring assembly may comprise at least one of the following: tachometer, accelerometer, potentiometer, resolver, encoder and imaging system. The monitoring assembly may be configured for measuring a time variation of a force or pressure. The monitoring assembly may comprise at least one of the following: a strain gauge, a load cell and a pressure sensor.

The monitoring assembly may comprise at least one pressure sensor operating to sense pressure between the force applying assembly and the object. The pressure sensors may be mounted in mutually perpendicular planes and to be at the same vertical level. The pressure sensors may include load cells.

According to yet another aspect of the invention, there is provided a control unit for use in a system for improving the object's motion, the control unit comprising:

an input utility for receiving data indicative of a measured motion of the object;

a memory utility for storing at least data indicative of a correct motion of the object;

a data processing and analyzing utility preprogrammed to analyze the received data indicative of the measured motion of the object, determining an error in the measured motion as a relation between said measured motion and said correct motion, to thereby enable generation of an operating signal to be used for operating a force applying assembly of the system so as to apply to the object an effecting force, said operating signal being such that the effecting force, when applied to the object, will increase a value of said error.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1A:
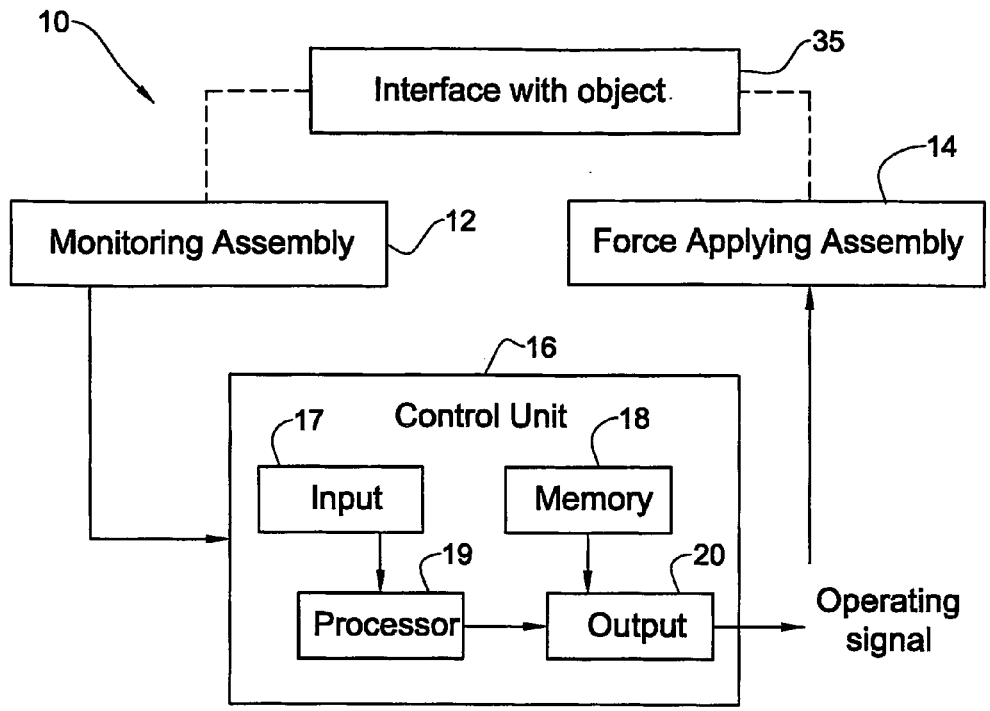
FIG. 1A is a schematic illustration of a motion improvement system according to the invention.

Referring to FIG. 1A, there is schematically illustrated a system for motion improvement 10 according to the invention. The system 10 comprises a monitoring assembly 12 for monitoring the motion carried out by the object, a force applying assembly 14, a control unit 16, which may be equipped with a data presentation unit (e.g., visual display or loudspeaker). Such a data presentation unit might be used not only for presenting the results but also for presenting information to the object to thereby direct his motion (e.g., operation information or virtual reality). The force applying assembly (and possibly also the monitoring assembly) is associated with an interface assembly 35 between the system and the object, whose motion is to be improved. The interface assembly 35 is preferably aimed at connecting the force applying assembly 14 to the object, but might also support the monitoring assembly 12 or a part thereof.

The monitoring assembly 12 includes a sensor or a plurality of sensors configured for identifying a measured motion carried out by an object (e.g., a patient, a pet, a machine) and generating data indicative thereof. The sensor(s) can detect specific motion of a limb, in particular, and evaluate motion parameters of a limb, in general. The sensor or sensors can be attached to the force applying assembly 14, and/or the interface assembly 35, and/or the object, or may be positioned at appropriate location(s) outside these assemblies. For example, the sensor(s) may be attached to the patient's limb or mounted in its vicinity so as to be capable of monitoring the limb motion. Such a sensor may for example include a light source attached to the limb and a CCD camera for continuously imaging the movement of the light source together with the limb. If the limb is attached to the force applying assembly 14 forming together a rigid unit, then the sensor may be attached to any location of this rigid unit. In a case a constant or known (in time and/or space) physical relation (e.g., transmission ratio) prevails between the limb and the force applying assembly 14, the sensor may be attached to any location of the force applying assembly 14. Generally, the sensor is selected in accordance with the motion parameter(s) to be monitored, and may include at least one of the following elements capable of detecting a position and measuring motion parameter(s): an encoder, resolver, potentiometer, tachometer, accelerometer, load cell, strain gauge, pressure transducer, torque sensor and imaging system.

The data indicative of the measured motion is received at the control unit 16 where this data is processed to determine an error in the measured motion and generate an operating signal for the force assembly 14. The operating signal is aimed at applying an effecting force to an object in order to improve the object's motion. According to the invention, this operating signal is such that the effecting force actually increases a value of the error. By this, the object (e.g., patient) is taught to correct by himself this specific kind of motion.

As shown in the figure, the control unit 16 includes a data input utility 17, a memory utility 18, a data processing and analyzing utility 19, and a data output utility 20. The data input utility 17 is configured for entering data into the control unit, such as data entered by user to be stored in the memory utility 18 and/or data coming from the monitoring assembly 12 to be received by the processor utility 19. The input utility may include a display panel, key board, touch screen, portable removable memory (discs, disc-on-key) etc., by which a user inputs data. It should be understood that the data input utility may be configured for receiving data from remote devices as well for transmitting received data to remote devices. This may include communication devices such as RS232-based components, e-mail utility, wireless communication hardware, or Infrared-based or Universal Serial Bus (USB)-based, input receiving components, and so on. The memory utility 18 stores certain reference data indicative of a predetermined correct motion for each kind of motions. The processor utility 19 is preprogrammed with suitable software based on a predetermined mathematical model capable of analyzing the measured motion-related data and determining a relation between this data and the corresponding reference data. This relation is indicative of an error in the measured motion. Upon determining the error, the processor utility 19 generates the operating signal to the force applying utility 14 to apply a certain effecting force to the object to thereby improve the object's motion. As indicated above, the operating signal is such that the effecting force increases a value of the error.

It should be understood that the processor utility may be the so-called "expert system" capable of carrying out a learning mode (e.g., using neural networks) and updating the reference data accordingly. For example, the measured motion profile of a limb, which is detected by the monitoring assembly and transferred to the processor utility 19 via the input utility 17, can be compared with the former motion profiles stored in the memory utility 18. The configuration may be such that, based on the data processing results, the processor utility 19 is capable of making a decision as to whether to generate a signal to operate the force applying assembly 14 to apply an effecting force to an object. In other words, the operating signal is generated only at certain circumstances or based on a certain condition of the measured motion. The generation of the operating signal may be based on any known suitable technique. This may for example be a technique utilizing preprogrammed conditioned alternatives: once a predetermined condition is met, the alternative is chosen. This method is commonly known as 'look-up table'. Another example is based on a learned or created decision using a neural networks system. The neural network can be a general algorithm or tailored specifically to a type of motion. The operating signal may contain sufficient parameters to cause a force to be applied to a limb. Such parameters may include the force magnitude, its components (if it is more than one-dimensional force), its duration, etc. It should be understood that both the control unit and the force applying assembly are configured for appropriate communication between them. The control unit 16 is preferably designed as an independent module compatible with various types of the force applying assembly and monitoring assembly.

In addition, the control unit 16 operates and controls a closed- or open-loop control over the force to be applied.

Either one of the open- and closed-loop controls is selected by the system operator based on relevant considerations. Such a loop may be formed only by the control unit 16 and the force applying assembly 14, or may also include the input from the monitoring assembly 12. This input for the closed-loop control may include data about the applied and former forces, characteristics of the object, and data about the object current and former motions. It may also include data about the interaction between the object and the force such as the resultant force between the object and the interface assembly 35.

The force applying assembly 14 is configured and operated to create and apply a force to an object. Additionally, it might enable an object to move within the predetermined freedom of movement of the force applying assembly 14, i.e., the object can move freely as far as it does not exceed the travel limits of the force applying assembly 14, even when the latter exerts a stronger (contra) force. A force applied by the force applying assembly 14 may act with, against or in other direction with respect to the object's motion direction (e.g., in an orthogonal direction to the object motion). It should be noted, although not specifically shown here, that the force applying assembly 14 includes a force generating unit. This may be a spring, weight, or electric motor (e.g., step motor, servo motor), which may be associated with a driver. The motor can be a linear or rotation motor. The force applying assembly may include a force transmission unit such as gear wheels; lever arrangement; or a hydraulic or pneumatic system including a cylinder with a piston, and an electric motor (which in this case would be the force generating unit), which produces, respectively, the oil and air pressure, resisting or enforcing the movement. As indicated above, the suitable interface 35 between the force applying assembly 14 and the object is preferably provided, to thereby enable bi-directional forces transmission, i.e., between the formers to the object and vice versa. In certain applications, where a freely movement of a limb is required, in appropriate dimensions, the interface is preferably designed such as to minimally disturb the limb during its motion.

The system 10 may include a display, which may be the monitor of the control unit or additional display, for the user or patient interface. Such a display can present targets for a patient to follow during his therapy, virtual reality scenes in one to three dimensions, as well as written instructions. These auxiliary means can facilitate the system operation as well as improve the achievements of the patient. The display is operated by the control unit 16, which can load it with stored information from the memory utility or from external sources (e.g., website, removable memory).

Figure 1B:
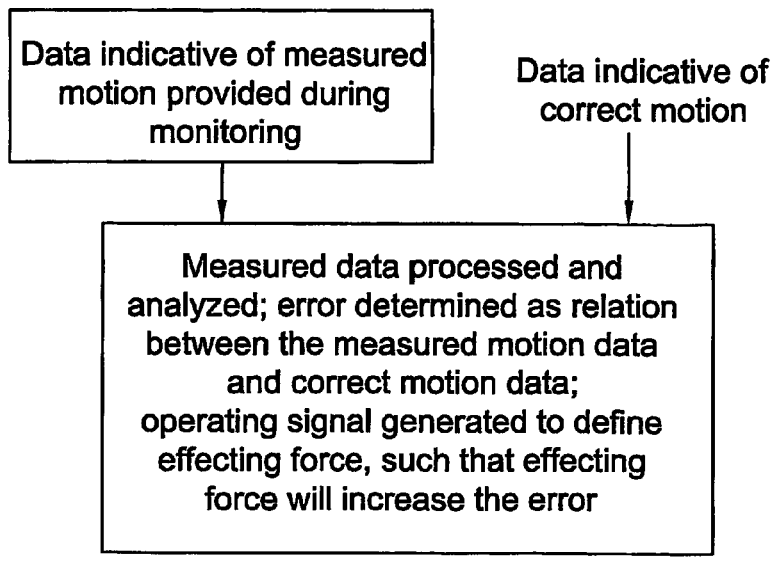
FIG. 1B is a flow diagram of a method according to the invention for improving the motion of an object.

FIG. 1B shows the main steps in the motion improvement method of the present invention. The object's motion is monitored, and data indicative of the measured motion is provided. The measured data is processed and analyzed using data indicative of a correct motion of the object. The processing is aimed at determining a relation between the data indicative of the measured motion and the data indicative of the correct motion, to thereby determine an error in the measured motion and generate an operating signal to be used to define an effecting force to be applied to the object. The operating signal is such that the effecting force, when applied to the object, increases the error value.

Figure 2A:
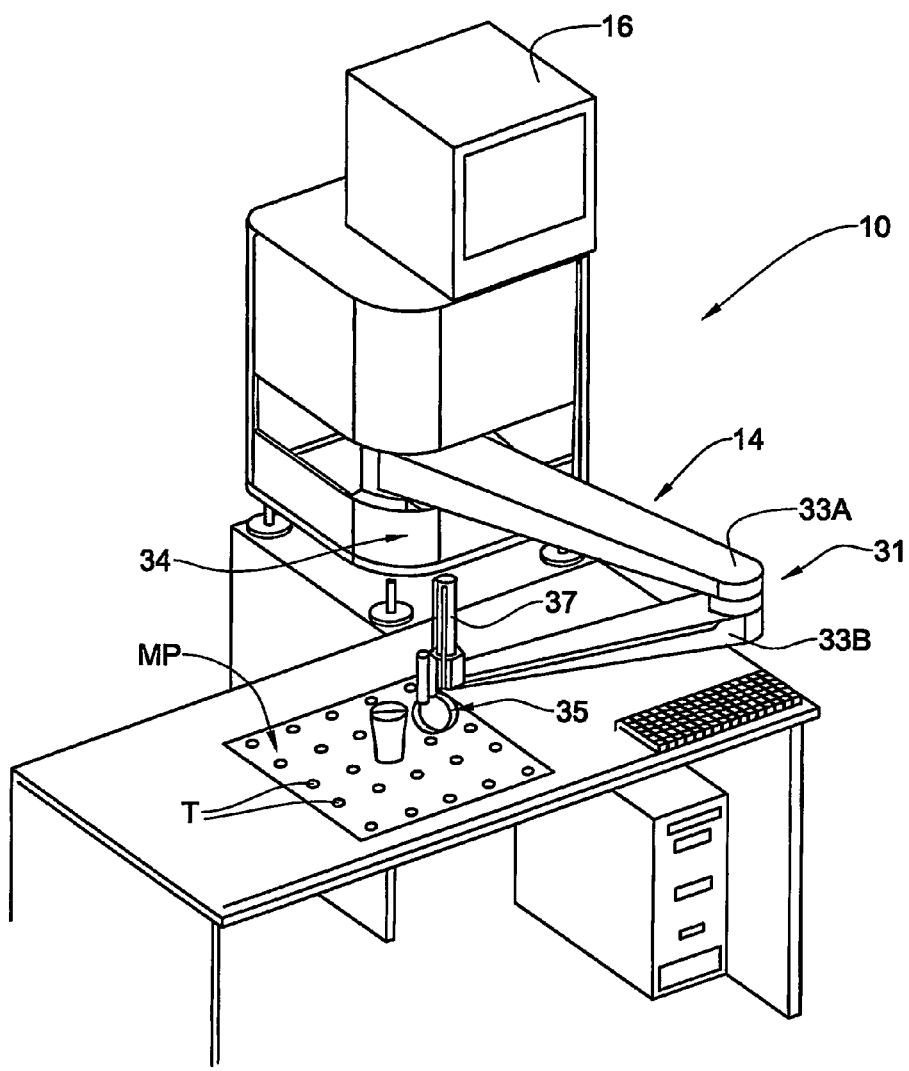
FIGS. 2A and 2B illustrate a specific, but non limiting example of the system of the invention.
Figure 2B:
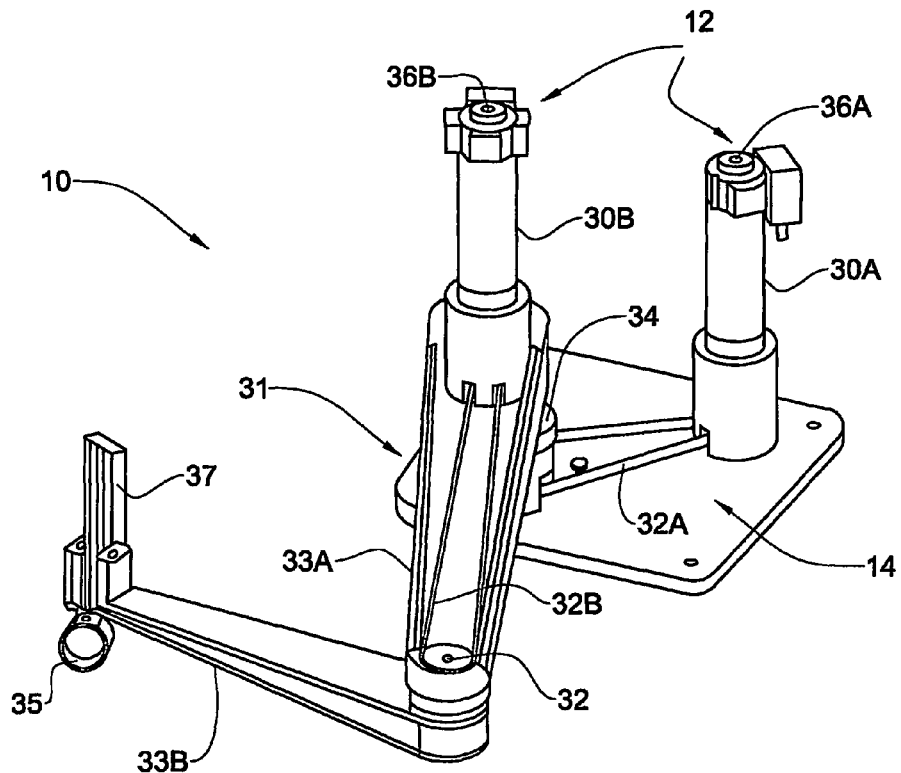

Referring to FIGS. 2A and 2B there is shown a specific but non-limiting example of a system 10 of the invention aimed at improving the motion of a patient's arm. The system 10 is configured to follow the patient's arm path during the motion of the arm, monitor (measure) this motion, and upon detecting an error in the measured motion, apply a required effecting force to the arm. As indicated above, the applied force is such as to increase a value of the error. The patient himself can move his arm freely or according to predetermined targets. The targets may be presented to him as a voice message or visual message (on a screen) as instructions like "MOVE YOUR ARM TO THE LEFT, THEN MOVE . . . ". Alternatively or additionally, as shown in the present example (FIG. 2A), a motion plane MP may be used below the patient's arm with targets T being marked on the motion plain. Such a motion directing assembly (e.g., screen, motion plane) may present virtual reality scenes, targets to follow, etc.

The system 10 has a monitoring assembly 12; a force applying assembly 14, and a control unit 16. As better seen in FIG. 2B, the monitoring assembly 12 includes two sensors in the form of encoders 36A and 36B mounted on shafts (not shown) of two motors 30A and 30B, respectively, that are associated with a lever arrangement 31. The force applying assembly 14 is formed by these two motors and the lever 31 arrangement. The motors present a force generating unit, and the lever arrangement 31 presents a force transmission unit. In the present example, the motors are preferably electric motors with rotating shafts. The lever arrangement 31 is associated with an arm holder element 35 that is preferably mounted on a guide element 37 to thereby allowing a patient to adjust his arm position on the lever arrangement. The arm holder 35 actually presents the interface between the object and the system. Possible configurations of the interface will be described more specifically further below.

The encoders 36A and 36B sense the movement of the lever arrangement 31 along two mutually perpendicular axes, respectively, caused by the movement of the patient's arm, and transmit the data indicative thereof to the control unit. The processor utility of the control unit analyzes this data and upon detecting an error, generates the operating signal to the motors 30A and 30B so as to apply to the patient's arm the effecting force increasing this error. The monitoring of the arm's motion and the control of this motion by the operating signal are carried out via the motors and lever arrangement in the following manner.

The lever arrangement 31 includes lever arms 33A and 33B pivotally connected to each other via a pin member 32. The lever arm 33A is mounted on a member 34, which is rotatable by motor 30A via a belt 32A, which is connected to the shaft of the motor 30A and to that of the member 34. Hence, the motor 30A initiates rotation of the member 34, and thus initiates pivotal movement of the arm 33A and 33B. The shaft of the motor 30B is in turn connected to the pin member 32 via a belt 32B, a force generated by the motor 30B being thereby transferred to the arm 33B that is connected to the interface 35 with the patient's arm. Thus, the operation of the motor 30A effects rotation of the member 34 and consequently pivotal movement of the arm 33A. The operation of the motor 30B effects rotation of the pin member 32 and consequently the pivotal movement of the arm 33B. In this way, any movement (force), along horizontal x-y plane can be effected with the interface 35 within the limits of the motors power and the dimensions of the force transmission unit. On the other hand, the current motion of the patient's arm along two mutually perpendicular axes is transferred to the encoders 36A and 36B via the lever arrangement and the motors' shafts. Additional sensors may be used, being attached to the interface 35, for monitoring the tensions and forces between the limb and the lever arm 33B as will be described below with reference to FIG. 3A.

It should be understood that the technique of the present invention provides also for the motion improvement of an automatic machine, especially where the machine does not perform accurate movement due to a lack of control, or a machine is to be upgraded and a tight control over movement is needed. In addition, automatic robots may be required to move from point to point or to follow a specific path in order to perform their tasks. The system of the present invention can be used to teach a robot to perform these movements while the robot is attached to the interface 35. The system can be used to stabilize a control system of non-stable systems such as common in military weapons and to simulate movement disorders. The system can be used to amplify the disorders by applying forces for example on a patient who suffers from such disorders. The patient's responses to such forces are monitored by the system, and the monitored data and input data, are analyzed to determine different forces to thereby enable to correct for the disorders.

Figure 3A:
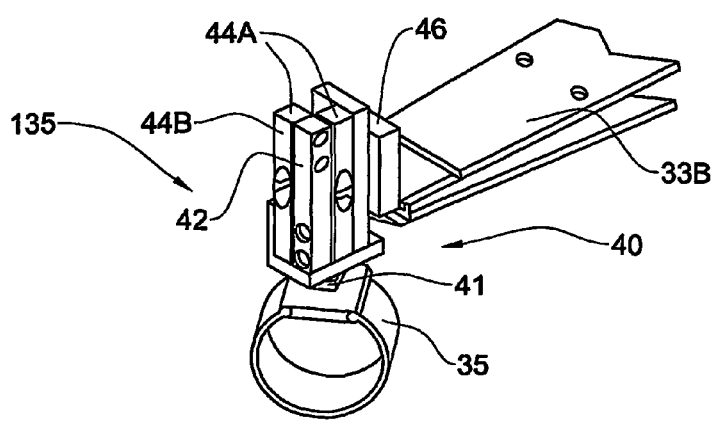
FIGS. 3A to 3C schematically illustrate several examples of an interface assembly between the system and an object, suitable to be used in the system of the present invention.
Figure 3B:
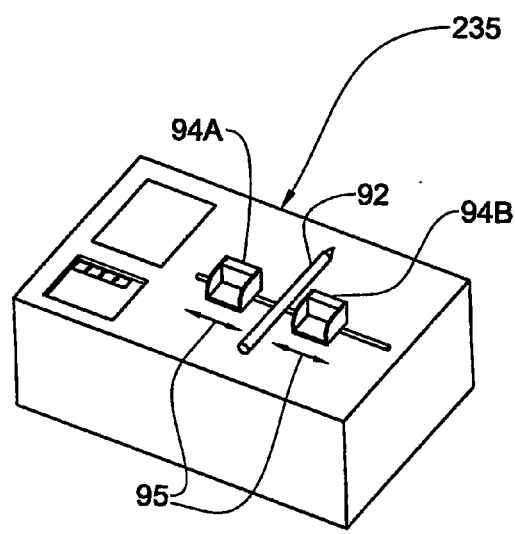
Figure 3C:
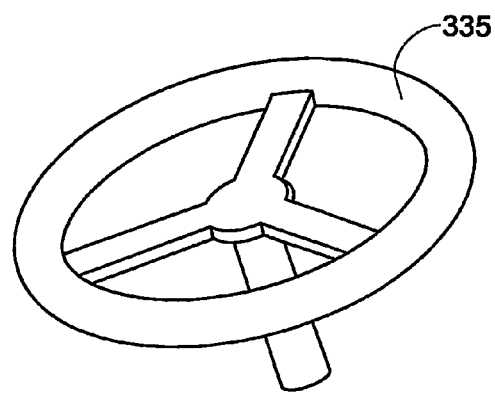

The interface assembly between the force applying assembly and the object may be of one of the following types:

a) "Following only" interface that enables solely attachment and force transmission to the object. The object is thus free to move, and the object's movement leads the interface, unless the force applying assembly 14 applies a force to the object. An example of such an interface assembly is shown in FIG. 3A. Here, the interface assembly 135 includes a ring 35 for enclosing and holding a patient's arm. The ring 35 is connected to the end of the lever arm 33B (i.e., to the force transmission unit) via a connecting arrangement 40. The latter includes a spherical bearing 41 directly coupled to the ring 35; brackets 42; and a plate 46 that is directly coupled to the arm 33B. The spherical bearing 41 enables three-dimensional movement of the patient's arm according to the patient's choice, in addition to the movement along the vertical axis by the sliding shaft (37 in FIG. 2B). Sensors (not shown) are also preferably provided being attached at appropriate location(s) between the lever arm 33B and the ring 35. In order to miniaturize the overall structure of the interface assembly, load cells 44A and 44B are used being connected to each other by the brackets 42 so as to be at the same vertical level and in mutually perpendicular planes. Such a structure ensures the detection of tensions and forces in two orthogonal directions, and in addition, saves the volume and reduces the potential flexibility.

b) "Interaction transfer" interface, that is used to enable interaction between a first object, whose movement should be improved, and a second object which is used to assist this task. FIG. 3B exemplifies such an interface assembly, generally designated 235. The interface assembly 235 is configured for assisting in teaching a patient to correctly use his fingers (constituting the first object) to perform a grasping operation, e.g., grasp a pencil 92 (constituting the second object). The interface assembly 235 includes two specially designed open cases 94A and 94B. The pencil 92 is positioned between the cases 94A and 94B. Each of these cases is moveable in a direction perpendicular to the pencil 92 as shown by arrows 95. The teaching is performed by letting the patient to enter two of his fingers, e.g., big toe and index finger, into the cases. Then, the patient may try grasping the pencil. The cases confine the motion. Sensors (not shown) are attached to the cases 94A and 94B and monitor the fingers movement. Consequently, the motion improvement system can apply a force to the fingers by moving either one or both of the cases 94A and 94B, all as described before. A similar interface may be used to teach a patient to press an object (second object) such as a button. Therefore, these are the "following only" interfaces with additional special characteristics: the interaction between the first and second objects takes place via this interface.

c) "Movement-enabling" interface, which enables the motion itself and in addition to allowing the interface to follow the object, allows for receiving and transferring forces from and to the object. Hence, the interface is needed to enable the motion, i.e., without such an interface no motion can be performed. As shown in FIG. 3C, such an interface assembly may include a driving wheel 335 held by patient hands and rotated by him. Additional example maybe the use of pedals of a bicycle, on which the patient legs are positioned and which are rotated by the patient legs.

Figure 4A:
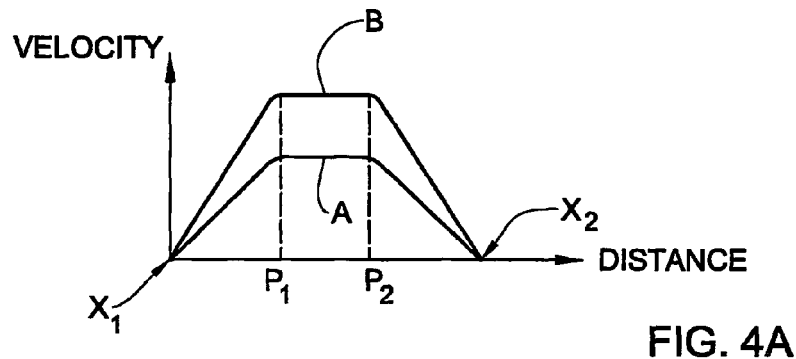
FIGS. 4A to 4C graphically illustrate the principles of the present invention for improving the object's motion.
Figure 4B:
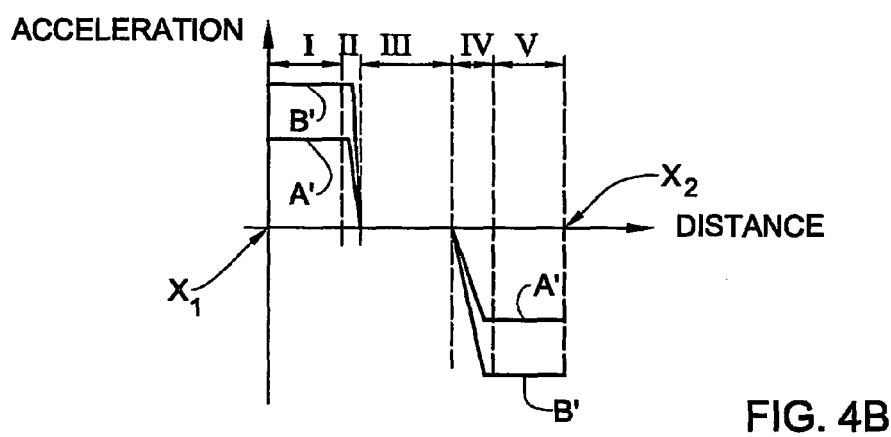
Figure 4C:
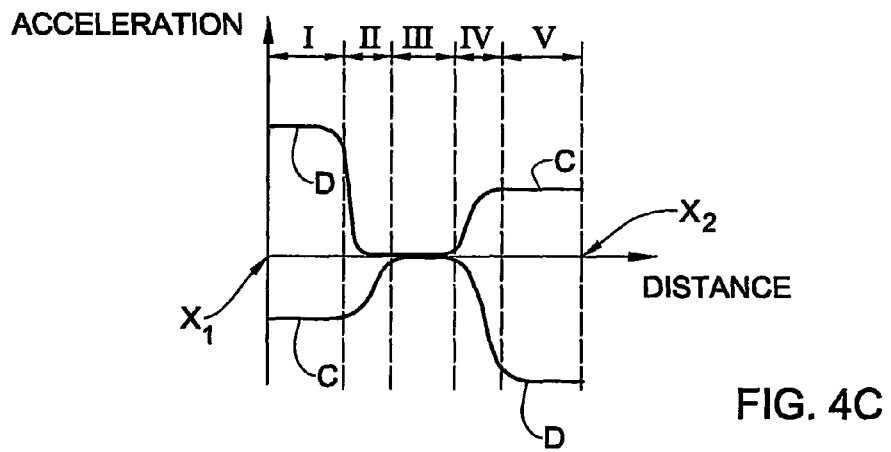

Reference is now made to FIGS. 4A-4C illustrating the principles of the present invention for the data processing and generation of the operating signal to improve the object's motion. In the present example, the motion considered is the motion of a patient's arm while holding a glass cup full with water and moving it from a position $X_1$ to a position $X_2$.

FIG. 4A describes the motion in the form of the motion velocity parameter as a function of the distance of movement. It should be noted that other parameters could be used as well, such as velocity vs. time. A starting point is set at the coordinate $X_1$. The relevant velocity profiles of the motion include a profile A, which is termed "ideal velocity profile", and profile B, which is the measured motion profile, namely, the actually measured motion of the patient's hand during a certain period of time $t_1$.

Profile A is a profile which describes the correct motion in such circumstances (i.e., for this specific type of motion). It can be an experimental profile constructed out of information gained as a result of experiments. For example, these may be experiments by which several individuals are asked to perform a similar motion. The results are averaged based on relevant parameter(s) such as age, sex, etc., and consequently the profile A is determined as the correct motion for specific circumstances (people who belong to certain age group, sex, etc.). Profile A could also be a theoretical profile derived from theoretical consideration. For example, the theoretical provide can be derived by experimenting a person moving such a cup, with no disorders. For the purpose of the example shown in FIG. 4A, the theoretical profile can be considered as that of the correct motion. Profile A could also be a combination of the experimental and theoretical derivation.

Profile B, which corresponds to the measured motion that is to be improved, could be measured by sensors configured and accommodated for detecting the motion along the motion path. In the present example, the motion velocity profile B is greater from the velocity profile A, in all the distance points, except for the starting and the finishing points $X_1$ and $X_2$. However, both profiles A and B have a similar pattern, namely, the motion velocity increases from the starting point $X_1$ until a certain point $P_1$, then remains stable up to a distance point $P_2$, and then decreases to zero at the finishing point $X_2$.

FIG. 4B shows profiles A' and B' corresponding to the time derivatives of the profiles A and B (i.e., motion accelerations), respectively, as a function of the same distance. The profiles A' and B' can be divided into five common segments: segment I corresponding to constant positive accelerations, segment II corresponding to positive decreasing accelerations, segment III corresponding to zero accelerations, segment IV corresponding to negative decreasing accelerations, and segment V corresponding to negative constant accelerations. According to this example, the absolute value of the current (measured) acceleration (profile B') is greater than the correct acceleration (profile A') at all the distances, except for that of segment III. Therefore, in this specific example the patient applies significantly excessive (extra) forces to perform this motion, and probably, the water will be spilled out of the cup. This of course may result with adverse effects such as disability to perform delicate motions, increased exhaustion and weariness and more. Hence, the so-determined error is indicative of an increased force applied by the patient.

FIG. 4C exemplifies a corrective one-dimensional acceleration profile D (profiles of an effecting force) to be applied to the patient's hand according to the present invention, as compared to an acceleration profile C that would applied according to the conventional motion improvement approach such as that implemented by system MIT-MANUS, commercially available from Interactive Motion Technologies, Inc. and described for example in the Internet Site http://www.interactive-motion.com/. The acceleration profile C is related to the positive difference between profile B' and profile A' of FIG. 4B (i.e., (A'-B')). So, according to the conventional approach, the effecting force is applied against the patient force, i.e., in such a way as to decrease the excess force (error) applied by the patient along the motion path. The acceleration profile D resulting from the operating signal of the present invention is different: profile D is related to a negative difference between profiles B' and A' (i.e., -(A'-B')), namely the effecting force is applied in such a way as to increase the difference (error) between the profiles B' and A'.

In general, various relations between the measured motion of an object to the correct motion may be used in the present invention, and are generally termed "Error". The Error is an indication to the relation between the two quantities. In the general case, the Error is a function of time and space coordinates, as well as the above-mentioned relation. Therefore, the Error is determined as:

$$\text{Error}(x_3, y_3, z_3, t_3) = f\{a(x_1, y_1, z_1, t_1), b(x_2, y_2, z_2, t_2)\}; \quad (1)$$

wherein $f$ is a function of $(x_i, y_i, z_i)$ that are space coordinates in an orthogonal or curvelinear coordinates system, $t_i$ is the time coordinate.; $a(x_1, y_1, z_1, t_3)$ and $b(x_1, y_1, z_1, t_3)$ are, respectively, the correct and measured motions (characterized by such parameter(s) as acceleration, velocity, etc.) of an object at certain space and time coordinates.

As shown by equation (1), the causes leading to the determination of the Error may originate at different (former) time and space coordinates from each other. In this respect, the Error may be a delay system. However, the general equation (1) can be degenerated in appropriate cases; for example, b will have the same time and space coordinates as the Error, while a may be time invariant (keeping in mind that a is a variable).

For example, the Error at time $t_2$ and space coordinates $x_2$, $y_2$, $z_2$ is defined as:

$$\text{Error}(x_2, y_2, z_2, t_2) = a(x_2, y_2, z_2) - b(x_2, y_2, z_2, t_2)\}; \quad (2)$$

wherein $a(x_2, y_2, z_2)$ is the correct acceleration of the object at the space coordinates $x_2$, $y_2$, $z_2$; and $b(x_2, y_2, z_2, t_2)$ is the measured acceleration at any time and space coordinates $x_2$, $y_2$, $z_2$.

According to this example, the Error$(x_2, y_2, z_2, t_2)$ is a fundamental property for the determination of the effecting force (i.e., its magnitude and direction).

The value of Error$(x_2, y_2, z_2, t_2)$ may be determined as follows: The current acceleration of the object at time $t_2$ and space coordinates $x_2$, $y_2$, $z_2$ is determined. To this end, the following data is given with respect to the specific object: its mass, the internal friction forces which are exerted during the object motion (i.e., within the object such as muscles friction, etc.), the interface of the force applying assembly, its mass, and its internal friction forces. For the purpose of this calculation, the interface attached to the object is considered in first order a rigid body. Then, the force equation (Newton's second law) is applied to the interface and the object, and consequently net acceleration (equivalent to measured acceleration) of the object $(a(x_2, y_2, z_2, t_2))$ is determined. In a second order, refinement for this calculation can be made using additional data about the internal forces between the interface and the object, eliminating the assumption of a rigid body. Such data can be obtained by suitable force or pressure meters mounted between the two (e.g., load cell 44A and 44B of FIG. 3A or active pressure transducers as will be exemplified further below).

The Error is determined by one of the following equations:

$$\text{Error}(x_2, y_2, z_2, t_2) = a(x_2, y_2, z_2, t_2)/b(x_2, y_2, z_2); \quad (3a)$$

$$\text{Error}(x_2, y_2, z_2, t_2) = \frac{a(x_2, y_2, z_2, t_2) - b(x_2, y_2, z_2)}{b(x_2, y_2, z_2)}; \quad (3b)$$

The effecting force $F_{applied}$ to be applied to the object at time $t_2$ and space coordinates $x_2$, $y_2$, $z_2$ is determined according to the following general force function:

$$F_{applied}(x_2, y_2, z_2, t_2) = f\{\text{Error}(x_2, y_2, z_2, t_2), CF_1, CF_2, SC, VC, FC, SF\}; \quad (4)$$

where $f$ is a function of $CF_1$ and $CF_2$, which are coefficients aimed at off-setting inertia and friction forces; SC, VC, and FC are the space, velocity and forces correction coefficients, respectively, aimed at correcting for errors in the monitoring assembly or the mutual influence of the monitoring assembly and the interface itself, or compensation for specific data of the object such as weight and dimensions; SF defines a safety upper-limit force to be applied, used for safety considerations such as to prevent damage to the object during the period it is connected to the interface, and in particular when the effective force is applied (e.g., prevention of limb breakage). The coefficients $CF_1$, $CF_2$, SC, VC, FC and SF are determined according to such object's parameters as velocity, sex, age, dimensions and weight. It should be noted that all these coefficients are expressed in force units.

The effecting force to be applied is preferably one of the following:

$$F_{applied}(x_2, y_2 z_2, t_2) = \min\begin{pmatrix} -k_1 \times [a(x_2, y_2, z_2, t_2) - b(x_2, y_2, z_2)] + CF_1 + CF_2 + \\ k_2 \times [x_2 - x_0] + k_3 \times [v_m - v_c] + k_4 \times [fm - fc], SF \end{pmatrix}; \quad (5)$$

wherein $k_1$ is positive, $k_2$-$k_4$ are either positive or negative factors, all based on, respectively, the object acceleration, the object's current position, the object's velocity and the frictions forces; $v_m$ and $v_c$ are respectively, the object's current and correct velocity at time $t_2$ and space coordinates $x_2$, $y_2$, $z_2$; $f_m$ and $f_c$ are respectively, the measured and correct forces; SF is the safety value, in force unit (if the effecting force is higher than SF it is likely that the object might be harmed by the interface).

The factors k may be determined in various ways. For example, they are determined in iterative procedures; from the first monitoring cycle to the next cycle, they are corrected, based on the detected information. According to another example, factor k is of the form $$k = \left(p - \min\left[\frac{c}{a}\right], p\right)$$

where p is constant, c is constant, and a is the measured motion of the object.

The control unit, which is either a stand alone unit or is a part of the system 10, continuously generates the operating signal in order to operate the force applying assembly. This signal is changed according to the result of calculations of the former equations.

The control unit may not generate such an operating signal unless a certain condition is fulfilled. An exemplary condition can be that the Error is above a predetermined threshold value. The threshold itself can be a constant, time-dependent, or the result of a neural network algorithm.

Therefore, the effecting force $F_{applied}$ is the minimum value between the safety-consideration coefficient SF and the above force expression (5): in order to prevent damage to object, the applied force should be limited, which is done by always imposing a maximal force to be applied, i.e., the min function. The first term in equation (5), $-k_1 \times [a(x_2,y_2,z_2,t_2) - b(x_2,y_2,z_2)]$, is considered the important term in the determination of the effecting force $F_{applied}$. This term is aimed at increasing the Error value, and consequently, the applied force. As a result, the difference between the object's measured motion and its correct motion is increased. This first term is preceded by (−) in equation (5) in order to emphasize that when it is added to the correct acceleration $b(x_2,y_2,z_2)$, the total acceleration (i.e., the effecting force) by which the objects moves is greater than the case when no (−) sign is preceded to it. Rest of the terms in equation (5) maybe of higher order or eliminated in various cases.

The effecting force may be calculated with a neural network algorithm taking into account specific data of the object such as its movement disorder characteristic (e.g., if this is a spastic patient), its weight, age, and sex.

Reference is now made to FIGS. 5A-5E and 6A-6E illustrating some more examples of the motion improvement system of the present invention.

Figure 5A:
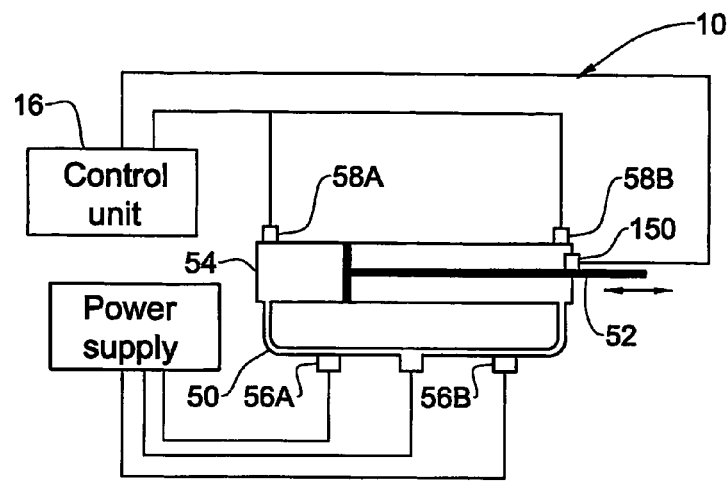
FIG. 5A schematically illustrates another example of the system of the present invention.

FIG. 5A shows a system 10 having a monitoring assembly 12, a force applying assembly 14, and a control unit 16. The force applying assembly 14 includes a hydraulic or pneumatic unit 50. The unit 50 includes a moveable piston 52 inside a cylinder 54 operated by liquid or air pumped by a motor (not shown) which is regulated by one or more valves 56A and 56B. Valves 56A and 56B are operated by a solenoid or additional motor (not shown). Two pressure transducers 58A and 58B are mounted at the two sides of the piston 52, and are aimed at measuring pressure used to evaluate forces between an interface and the object.

The monitoring system 12 includes a linear encoder 150 mounted at the exit of piston 52 and operated to measure the piston movement. The monitored data is processed by the control unit 16 in order to determine the object motion parameter via the motion of the piston 52.

Figure 5B:
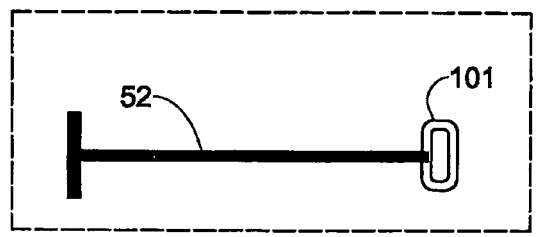
FIGS. 5B to 5E exemplify configurations of the force transmission units and interface assemblies suitable to be used in the system of FIG. 5A.

As shown in FIG. 5B, the piston 52 may be directly connected to a practice handle 101 that is held by the patient who practices a linear motion that is to be controlled and, if needed, improved. The handle 101 presents a "movement-enabling" interface.

Figure 5C:
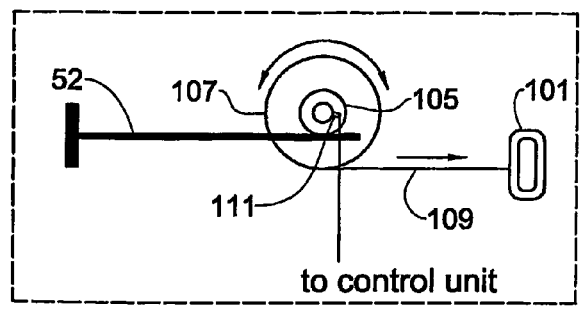

As shown in FIG. 5C, a wheel arrangement is connected to the piston 52. The wheel arrangement includes first and second wheels 105 and 107 mounted on a common shaft. The wheel 105 is mounted on the piston 52. Provided on the circumference of the wheel 107 is a cable 109 extending from the wheel 107 to the handle 101. A linear motion of the piston 52 thus effects the rotation of the wheel 105, which in turn effects the rotation of the wheel 107, and as a result effects the motion of the cable 109 connected to the handle 101 held by the patient who practices a linear motion. An encoder 111 is attached to the wheel 105 for measuring the motion of this wheel.

Figure 5D:
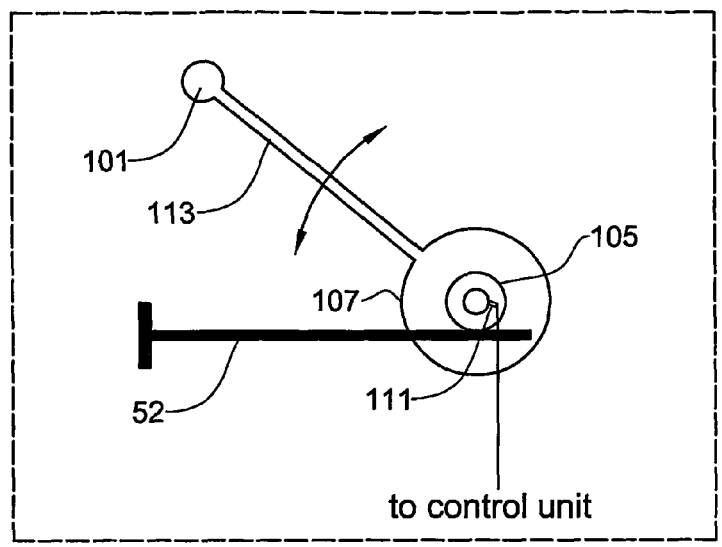

FIG. 5D exemplifies the use of a rigid connector (stick) 113 between the wheel 107 and the handle 101 (instead of the cable 109 of FIG. 5C), in order to practice the rotational motion.

Figure 5E:
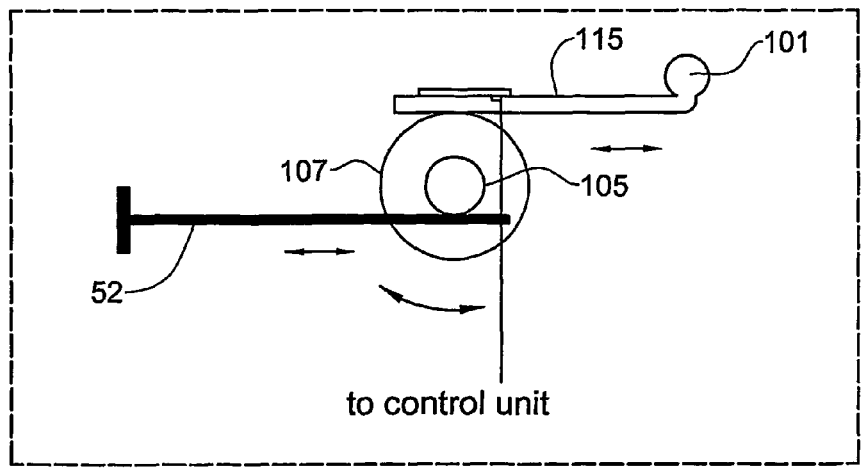

In the example of FIG. 5E, the effecting force is directly transmitted to and monitored through the motion of a rigid linear connector 115 between the wheel 107 and the handle 101 while controlling a linear motion practiced by the patient.

Figure 6A:
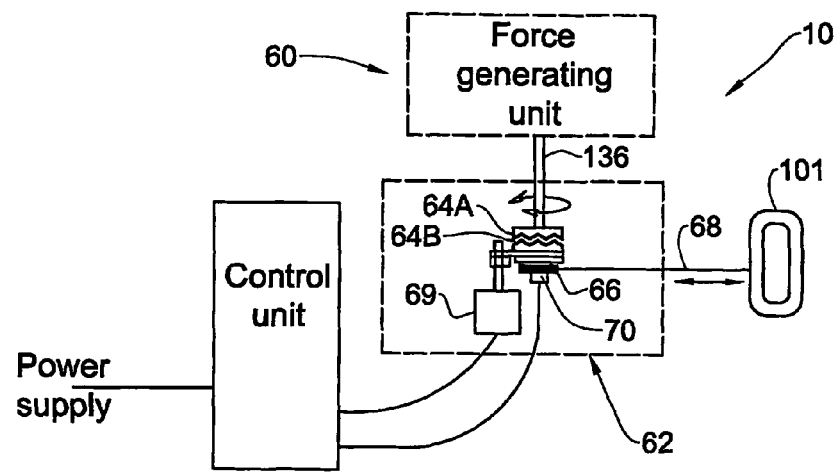
FIG. 6A schematically illustrates yet another example of the system of the present invention.
Figure 6B:
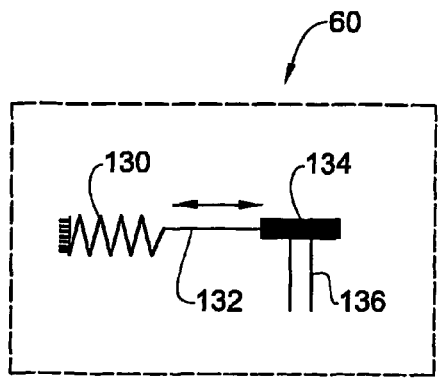
FIGS. 6B to 6D show three examples, respectively, of a force generating unit suitable to be used in the system of FIG. 6A.
Figure 6C:
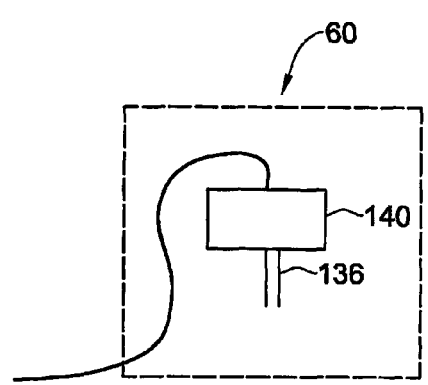
Figure 6D:
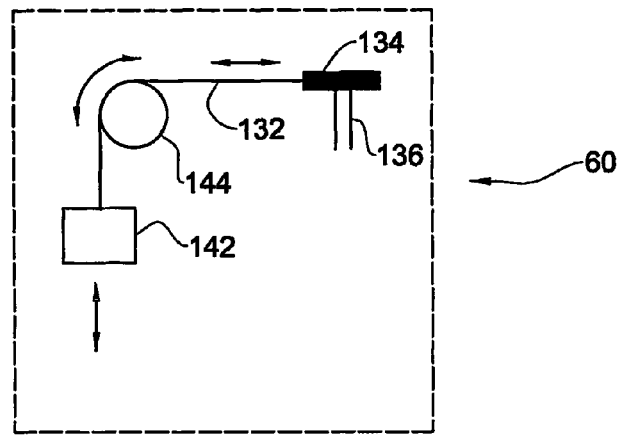

FIG. 6A illustrates a system 10 utilizing a force applying assembly 14 with a force generating unit 60 and a force transmitting unit 62 which is connected to a member 101 (interface assembly) handled by a user while carrying out a linear motion. Examples of the force generating unit 60 are shown in FIGS. 6B-6D. The force generating unit 60 is connected to the force transmitting unit via a rotatable member 136

The force transmission unit 62 includes a friction clutch 64 which transmits the motion from the force generating unit 60 to a rotating pulley 66 surrounded by a pulling cable 68 connected to the handle 101. The clutch 64 is composed of two discs 64A and 64B, which faces each other by identically patterned surfaces. The disc 64A is mounted on the distal end of the rotatable member 136, while the disk 64B is mounted on the pulley 66. The clutch 64 (its disc 64B) is regulated by a; motor or solenoid 69 via a lead screw (not shown) which effects the motion of one side of the clutch 64 (the disc 64B) against his second side (disc 64A), thus increasing or decreasing the friction between the discs 64A and 64B. As a result, the motion of the pulley 66 is controlled. The monitoring assembly includes an encoder 70 mounted on the pulley 66 to measure its displacement. The force generating unit 60 and the force transmitting unit 62 are operated by the control unit 16. Data generated by the encoder 70 is transmitted to the control unit.

As shown in FIG. 6B, the force generating unit 60 includes an active spring 130 which affects a linear motion. This linear motion is transmitted by a cable 132 to a pulley 134 mounted on the member 136. By this, the rotation of the pulley 134 is transferred to the member 136 and accordingly to the disc 64A, which becomes in contact with the disc 64B initiated either by the movement of the handle 101, i.e., by user, or by the motor 69, i.e., by the control unit.

According to the example of FIG. 6C, the force generating unit 60 is an active motor which directly rotates the member 136.

In the example of FIG. 6D, the force generating unit 60 is generally similar to that of FIG. 6B, but distinguishes therefrom in that instead of using an active spring (130 in FIG. 6B), a pulley 144 is used being loaded with a mass 142 via a pull cable 132.

Figure 6E:
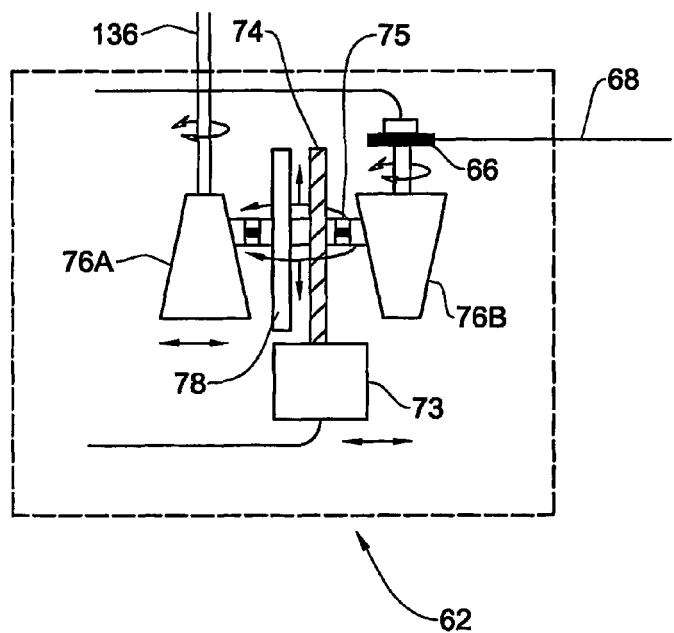
FIG. 6E shows an example of a force transmitting unit suitable to be used in the system of FIG. 6A.

As shown in FIG. 6E, the force transmission unit 62 may be composed of a continuous gear. This is implemented by using a first conical wheel 76A connected to the force generating unit 60 via member 136 and rotated by this member, a second conical wheel 76B, and a transmission wheel 75 located between the two wheels 76A and 76B. Any rotation of the conical wheel 76A will thus cause the rotation of the transmission wheel 75 which in turn, will rotate the second conical wheel 76B. The second conical wheel 76B rotates the pulley 66 and the cable 68 as described above with reference to FIG. 6A. A mechanism by which the force transfer ratio between the conical wheels 76A and 76B is determined and effected utilizes an additional motor 73 that rotates a lead screw 74 to which the transmission wheel 75 is attached. As a result, any rotation of the lead screw 74 affects the motion of the wheel 75 along a leading axis 78. It should be noted that instead of using the motor 73 and screw 74, a solenoid could be used.

Therefore, by locating the wheel 75 in a certain position the force transmission ratio can determined.

It should be understood that the present invention may advantageously be used in a butterfly machine or the like system including a weight lifting in a way that exerts a variable moment along a rotatable lever which changes the moment due to a change in the angle between the lever and the gravitation force axis. Such a buttery machine utilizing the present invention includes a spring-based assembly configured to be shiftable between its folded and extended positions, with a spring tension force being decreased during the shifting, rather than being increased as in the conventional machine.

Those skilled in the art will readily appreciate that various modifications and changes can be applied to the embodiments of the invention as hereinbefore exemplified without departing from its scope defined in and by the appended claims. The monitoring and force applying assemblies may be of any known suitable type allowing for, respectively, measuring the current motion of an object, and applying a force affecting this motion. The data processing and analyzing utility may run any suitable algorithm allowing for determining a relation between the measured motion and the correct motion thus determining an error in the measured motion, and allowing for determining an optimal effecting force, which when applied to the object increases the value of error.

The invention claimed is:

1. A method for improving an object's motion, the method comprising:
   providing a data processing and analyzing utility;
   processing, in the data processing and analyzing utility, data indicative of a measured motion of the object and determining a relation between the measured motion and a predetermined correct motion, the relation representing an error in the measured motion;
   generating an operating signal that is responsive to the relation representing said error in said measured motion, wherein the operating signal defines an effecting force to be applied to the object for increasing a value of the error; and
   applying to the object the effecting force as defined by the operating signal, which effecting force is of a magnitude and direction to increase the value of the error.

2. The method of claim 1, wherein said processing data comprises, upon determining said error, determining whether a certain predefined motion condition is satisfied with respect to said error, to thereby generate said operating signal if said condition is satisfied.

3. The method of claim 1, wherein applying to the object the effecting force as defined by the operating signal causes the object to initiate a negative motion in response to the increased value of the error, thereby resulting the motion of the object approaching said correct motion.

4. The method of claim 1, wherein said error is indicative of a difference between said correct and said measured motion.

5. The method of claim 1, wherein said error is indicative of a ratio between said correct and said measured motion.

6. The method of claim 1, wherein said effecting force is a resistive force only.

7. The method of claim 1, comprising providing the data indicative of the correct motion of the object.

8. The method of claim 7, wherein the provision of said data indicative of the correct object's motion comprises providing a database including the correct motion data for various types of motions.

9. The method of claim 1, wherein the effecting force is calculated by taking into account at least one physical parameter of the object, whose motion is to be improved.

10. The method of claim 9, wherein said at least one physical parameter includes at least one of the object's weight and dimension.

11. The method of claim 1, wherein the correct object's motion is indicative of at least one physical parameter of said object, whose motion is to be improved.

12. The method of claim 11, wherein said at least one physical parameter includes at least one of the object's weight and dimension.

13. The method of claim 1, comprising analyzing the data indicative of the measured motion to update the data indicative of the correct object's motion.

14. The method of claim 1, comprising monitoring the object's motion, wherein said monitoring of the object's motion is carried out while substantially unaffecting the data indicative of the measured motion.

15. The method of claim 1, comprising monitoring the object's motion, wherein said monitoring provides a known effect on the data indicative of the measured motion, said processing taking into account said known effect while determining the relation between said measured motion and said correct motion.

16. The method of claim 1, comprising providing an interface assembly between the object and a motion improvement system that includes monitoring and force applying assemblies.

17. The method of claim 16, wherein said interface assembly is configured for holding the object whose motion is to be improved.

18. The method of claim 16, wherein said interface assembly is configured for substantially unaffecting the data indicative of the measured motion.

19. The method of claim 16, wherein said interface assembly is configured for applying a known effect on the data indicative of the measured motion, said processing taking into account said known effect while determining the relation between said measured motion and said correct motion.

20. The method of claim 16, wherein said interface assembly is configured to be operable in first and second modes, when operating with the first mode the interface assembly affecting the motion of the object, and when operating with the second mode the interface assembly following the object's motion.

21. The method of claim 16, wherein the interface assembly is configured and operable to enable the object to conduct the motion.

22. The method of claim 16, wherein the interface assembly is configured and operable to transfer forces between the object, whose motion is to be improved, and a second object.

23. The method of claim 1, comprising providing motion directions for the object, whose motion is to be improved.

24. The method of claim 1, wherein the operating signal defines at least one of one-dimensional, two-dimensional, and three-dimensional vectors of the effecting force.

25. The method of claim 1, wherein said effecting force is determined as a minimum between certain first and second force values, wherein the first force value is determined as a safety upper-limit force applicable to the object while preventing damage to the object, and the second force value is defined by the error so as to cause the increase of said error.

26. A method for improving an object's motion, the method comprising:
   (a) providing data indicative of a correct motion of the object;

(b) providing a data processing and analyzing utility;
(c) monitoring the motion of the object and generating data indicative of a measured motion;
(d) processing, in the data processing and analyzing utility, the generated data and determining a relation between said measured motion and said correct motion, said relation representing an error in said measured motion;
(e) analyzing the determined error and generating an operating signal that is responsive to the relation representing said error in said measured motion, wherein the operating signal defines an effecting force to be applied to the object for increasing a value of said error; and
(f) applying to the object the effecting force as defined by the operating signal, which effecting force is of a magnitude and direction to increase the value of said error.

27. A system for use in improvement of an object's motion, the system comprising:
(a) a monitoring assembly configured and operable for monitoring a motion of the object and generating data indicative of the measured motion;
(b) a force applying assembly configured and operable to apply a force to the object;
(c) a control unit having a memory utility for storing data indicative of a correct motion of the object; and a data processing and analyzing utility preprogrammed to:
    (1) analyze the data generated by the monitoring assembly,
    (2) determine any error in the measured motion as a relation between the measured motion and the correct motion,
    (3) generate an operating signal in response to the determined error to be used for operating the force applying assembly to apply an effecting force to the object, said operating signal defining the effecting force to be applied to the object for increasing a value of said error, and
    (4) apply the operating signal to said force applying assembly to cause said force applying assembly to apply to the object the effecting force as defined by the operating signal, which effecting force is of a magnitude and direction to increase the value of the error.

28. The system of claim 27, comprising an interface assembly interconnected between said force applying assembly and the object.

29. The system of claim 27, wherein the monitoring assembly is configured for measuring a time variations of a position of the object.

30. The system of claim 29, wherein the monitoring assembly comprises at least one of the following: tachometer, accelerometer, potentiometer, resolver, encoder and imaging system.

31. The system of claim 27, wherein the monitoring assembly is configured for measuring a time variation of a force or pressure.

32. The system of claim 31, wherein the monitoring assembly comprises at least one of the following: a strain gauge, a load cell and a pressure sensor.

33. The system of claim 27, wherein the monitoring assembly comprises at least one pressure sensor operating to sense pressure between the force applying assembly and the object.

34. The system of claim 33, wherein the pressure sensors are mounted in mutually perpendicular planes and are at the same vertical level.

35. The system of claim 33, wherein the pressure sensors include load cells.

36. The system of claim 28, wherein said interface assembly is configured for holding the object whose motion is to be improved.

37. The system of claim 28, wherein said interface assembly is configured for substantially unaffecting the data indicative of the measured motion.

38. The system of claim 28, wherein said interface assembly is configured for applying a known effect on the data indicative of the measured motion, said data processing and analyzing utility being preprogrammed to take into account said known effect while determining the relation between said measured motion and said correct motion.

39. The system of claim 28, wherein said interface assembly is configured to be operable in first and second modes, when operating with the first mode the interface assembly affecting the motion of the object, and when operating with the second mode the interface assembly following the object's motion.

40. The system of claim 39, wherein the interface assembly is configured and operable to enable the object to conduct the motion.

41. The system of claim 39, wherein the interface assembly is configured and operable to transfer forces between the object, whose motion is to be improved, and a second object.

42. The system of claim 27, comprising a motion directing arrangement presenting motion instructions to a user, whose motion is to be improved.

43. The system of claim 27, wherein said relation is determined as a difference between said correct motion and said measured motion.

44. The system of claim 27, wherein said relation is determined as a ratio between said correct and said measured motion.

45. The system of claim 27, wherein said effecting force is a resistive force only.

46. A control unit for use in a system for improving an object's motion, the control unit comprising:
an input utility for receiving data indicative of a measured motion of the object;
a memory utility for storing at least data indicative of a correct motion of the object;
a data processing and analyzing utility preprogrammed to analyze the received data indicative of the measured motion of the object, said data processing and analyzing utility being operative for: determining an error in the measured motion as a relation between said measured motion and said correct motion, and, generating an operating signal that is responsive to the relation representing the determined error, wherein the operating signal is used for operating a force applying assembly of the system so as to apply to the object an effecting force as defined by the operating signal, which effecting force is of a magnitude and direction to increase a value of said error.

* * * * *